United States Patent
Provonchee et al.

(10) Patent No.: US 6,328,870 B1
(45) Date of Patent: Dec. 11, 2001

(54) ELECTROPHORESIS GEL RUNNING PLATE

(75) Inventors: Richard Provonchee, Cushing, ME (US); Narendra Vartak, Coppell, TX (US)

(73) Assignee: CBM Intellectual Properties, Inc., Reno, NV (US)

( * ) Notice: Subject to any disclaimer, the term of this patent is extended or adjusted under 35 U.S.C. 154(b) by 0 days.

(21) Appl. No.: 09/491,917

(22) Filed: Jan. 27, 2000

(51) Int. Cl.$^7$ .................................................. G02N 27/26
(52) U.S. Cl. ............................................ 204/616; 204/466
(58) Field of Search ................................. 204/450, 456, 204/466, 469, 600, 606, 609; 206/569, 205, 557; 220/796, 200; 422/50, 61, 58; 99/451, 358, 428

(56) References Cited

U.S. PATENT DOCUMENTS

| | | | |
|---|---|---|---|
| 4,314,897 | 2/1982 | Monte et al. | 204/449 |
| 5,074,981 | 12/1991 | Fairfield | 204/466 |
| 5,085,758 | 2/1992 | Guadagno et al. | 204/449 |
| 5,148,607 * | 9/1992 | Lasiter | 33/549 |
| 5,149,418 | 9/1992 | Flesher | 204/618 |
| 5,217,593 | 6/1993 | MacConnell | 204/451 |
| 5,443,704 | 8/1995 | Kirkpatrick et al. | 204/620 |
| 5,549,806 | 8/1996 | Chen | 204/621 |
| 5,709,788 | 1/1998 | Chen | 104/619 |
| 5,837,288 | 11/1998 | Sylvester et al. | 424/484 |
| 5,904,826 | 5/1999 | Chen | 204/616 |

OTHER PUBLICATIONS

Asaro et al., "Modified apparatus for voltage gradient gel electrophoresis", *Journal Of Chromatography A*, 855 (1999) 7723–726.

* cited by examiner

*Primary Examiner*—Jill Warden
*Assistant Examiner*—Alex Naguerola
(74) *Attorney, Agent, or Firm*—Drinker Biddle & Reath LLP

(57) ABSTRACT

A gel running plate for use in an electrophoresis process to cover an electrophoresis gel positioned within a tray. The gel running plate adapted to effect flow of electrical current into and out of the tray. The gel running plate having a length less than a length of the tray such that a gap exists between the tray and the plate when the plate is positioned on the tray. The gel running plate also having a width at least as wide as the width of the tray such that the plate rests upon the tray when the plate is positioned on the tray.

30 Claims, 6 Drawing Sheets

ELECTROPHORESIS GEL RUNNING PLATE

FIELD OF THE INVENTION

The present invention relates to the field of electrophoresis and, more particularly, to running and hold-down plates for use in retaining an electrophoresis gel in place during an electrophoresis process.

BACKGROUND OF THE INVENTION

Gel electrophoresis is a process that has long been in use for clinical diagnosis and laboratory research. It is based upon the principle that electrically charged biological macromolecules will migrate through a solvent medium when subjected to an electrical field. Since macromolecules may vary in molecular weight and charge, it is possible to use an electrophoresis process to distinguish between different macromolecules based on their respective rates of movement through the solvent. Electrophoresis can also be used for other types of macromolecular analysis, such as detecting amino acid changes.

In a common form of gel electrophoresis, the gel solution is cast and solidifies into a thin planar slab gel. The samples being tested are placed within cavities or wells formed within the electrophoresis gel. The gel is then placed in a buffer solution within an electrophoresis gel chamber. A current is applied to the buffer solution causing the biological macromolecules to migrate through the gel.

Originally, the laboratories conducting the testing mixed the gel solution and cast their own gel slabs on-site. It soon became apparent, however, particularly as electrophoresis testing of DNA increased, that it is more convenient and more precise to use precast gel slabs made to uniform composition, size and configuration standards. The most common precast gel slab has a thin planar rectangular shape and includes a series of spaced wells which receive the biological samples being investigated. Conventional gel slabs are inherently flimsy and subject to tearing and deformation if not handled carefully. A particularly sensitive area in the gel is the thin walls separating the sample wells. While any deformation or tearing of the gel slab creates some risk of producing inaccurate results, a breach between wells allowing commingling of adjacent biological samples could generate erroneous results.

In many cases, the precast gel slabs are supplied in a package that cannot be placed directly into the gel chamber or which does not include a convenient mechanism for holding the gel submerged under the buffer solution within the gel chamber. Since the gel is nearly the same density as the buffer solution, small movements of the chamber can easily cause the gel to shift. Also, any slight movement of the overlaying buffer solution can cause the gel to shift. The motion of the buffer solution can be caused by thermal gradients produced in the buffer by the electric current, or by bubble generation in the buffer.

One method that has previously been used to anchor the gel involves a backing sheet adhesively attached to a flat surface of the slab. The sheet extends beyond the edges of the slab to form a narrow overhang of sheet along the sides of the slab. A plastic anchor having two long thin beams, connected at the ends and having a thin bridge in the middle, is placed over the slab such that the long beams rest on the sheet overhang. The device is sold under the brand name "Catamaran". The Catamaran type anchor, however, anchors the backing sheet rather than the gel directly. As such, if the gel slab becomes dislodged from the backing sheet when power is switched to the electrodes, the slab will float in the buffer liquid and cause a loss of sample from the wells or skewed electrophoretic patterns. In addition, the plastic backing sheet adhered to the gel precludes transfer of DNA to a solid support such as a nylon membrane, and can make DNA recovery more difficult.

Other than the Catamaran anchor described above, the object frequently used to anchor the bare slab is usually some handy laboratory device selected ad hoc, such as a glass rod or glass plate that is placed across a portion of the slab. While this is a practical solution, it is clearly not an optimal one, since such devices often cause distortions in the migration of macromolecules through the gel by interfering with the electrical field.

Another device recently developed to hold down a gel slab during an electrophoresis process is an anchor disclosed in co-pending application Ser. No. 09/178,218, entitled "Anchor for Electrophoresis Gel", filed Oct. 23, 1998. The anchor includes a plurality of supporting members (legs) which extend downward from a frame. The supporting members are positioned so as to rest on the top of the gel during the electrophoresis process.

Recently there has been an increase in the use of trays for supporting and transporting electrophoresis gels. These trays are typically placed within the chamber electrophoresis. While the trays provide a suitable mechanism for protecting the electrophoresis gel from damage, they increase the chances of developing artifacts in the gel. In particular, the use of a tray during an electrophoretic run can produce an effect known as "hourglassing", as well as result in the appearance of tilted bands in the gel. A schematic top view of an electrophoretic process is illustrated in FIG. 1. A gel 2 is shown positioned within a tray 4. Lines 6 graphically represent the electrical field flowing through the buffer and gel from one side to the other (e.g., left to right). The flow of the electric current over the side walls $4_S$ of the tray 4 about midway along the length of the tray is wavy, as shown. As a consequence, the gel is subjected to non-parallel field lines in this area producing an hourglass shaped distortion in the sample lanes.

A similar phenomenon occurs in the front and back of the gel as the electric field passes over the front and back edges $4_F$, $4_B$ of the tray 4. Referring to FIGS. 2, a schematic partial cross-sectional view of the tray is shown depicting the electrical fields generated over the front edge $4_F$ during an electrophoresis process. This flow pattern results in an uneven current flow through the gel resulting in the samples traveling slower along the bottom of the gel than the top. As a consequence, the samples produce tilted bands (often perceived as fuzzy bands). Although the uneven current flow tends to diminish as the current flows through the gel, the cant introduced at the front of the tray continues through the whole gel.

Another problem with conventional trays is that they generally have the same density as the buffer solution and, thus, the same drifting problems described above associated with the gels can also occur with the use of trays.

A need, therefore, exists for an improved device for holding a gel in place during an electrophoresis process and which device minimizes inaccuracies caused by hourglassing and tilted bands.

SUMMARY OF THE INVENTION

One object of the invention is to provide a gel running plate for use in an electrophoresis process which improves the accuracy of the resulting data.

Another object of the invention is to provide a gel running plate for use in an electrophoresis process which controls the electrical current flow into and out of a tray containing an electrophoresis gel.

These and other objects and advantages are provided by the gel running plate according to the present invention. The gel running plate is intended for use in an electrophoresis process to cover an electrophoresis gel positioned within a tray. The gel running plate is adapted to effect flow of electrical current into and out of the tray. The gel running plate has a length that is less than the length of the tray such that gaps exist between the front and back of the gel running plate and the tray when the gel running plate is positioned on the tray.

The gel running plate also has a width that is at least as wide as the width of the tray so that the gel running plate rests upon the side walls of the tray when the plate is positioned on the tray.

In one embodiment of the invention, gaskets are added between the gel running plate and the side walls of the tray to provide an improved electrical seal between the two components.

In another embodiment, the gel running plate is designed to support the tray off the floor of the chamber to improve cooling of the gel.

The foregoing and other features and advantages of the present invention will become more apparent in light of the following detailed description of the preferred embodiments thereof, as illustrated in the accompanying figures.

BRIEF DESCRIPTION OF THE DRAWINGS

For the purpose of illustrating the invention, the drawings show a form of the invention which is presently preferred. However, it should be understood that this invention is not limited to the precise arrangements and instrumentalities shown in the drawings.

DETAILED DESCRIPTION OF THE EMBODIMENTS

While the invention will be described in connection with one or more preferred embodiments, it will be understood that it is not intended to limit the invention to those embodiments. On the contrary, it is intended that the invention cover all alternatives, modifications and equivalents as may be included within its spirit and scope as defined by the appended claims.

Figure 1:
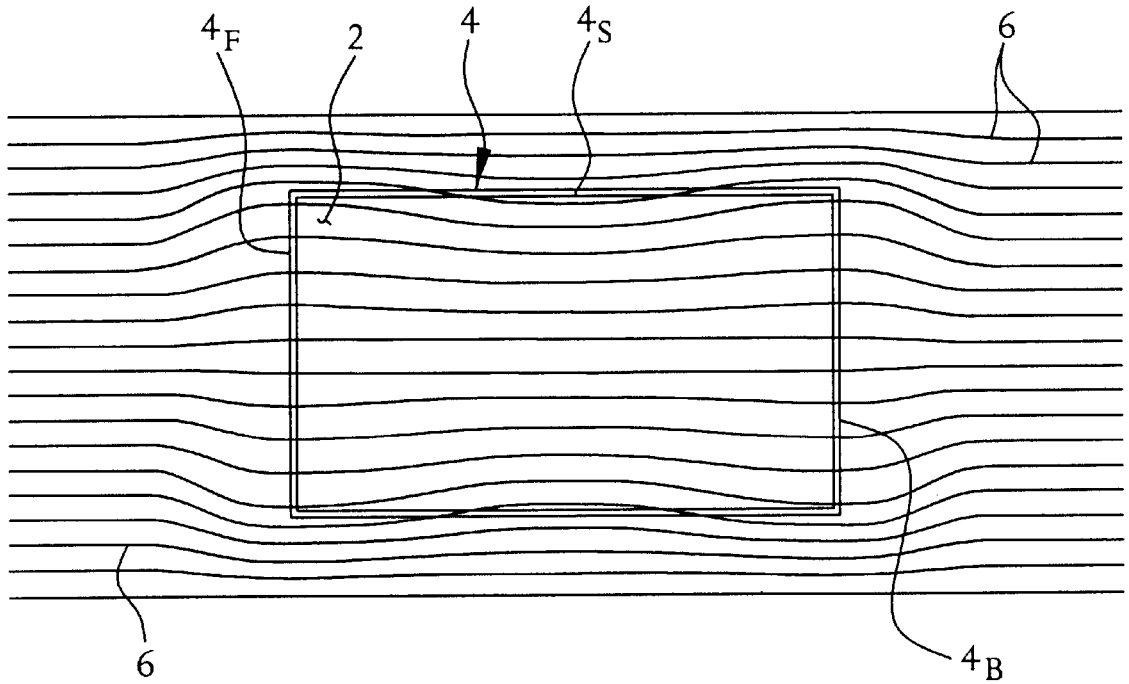
FIG. 1 is schematic plan view of an electrophoresis process illustrating the electrical field flow around a conventional tray containing a gel.
Figure 2:
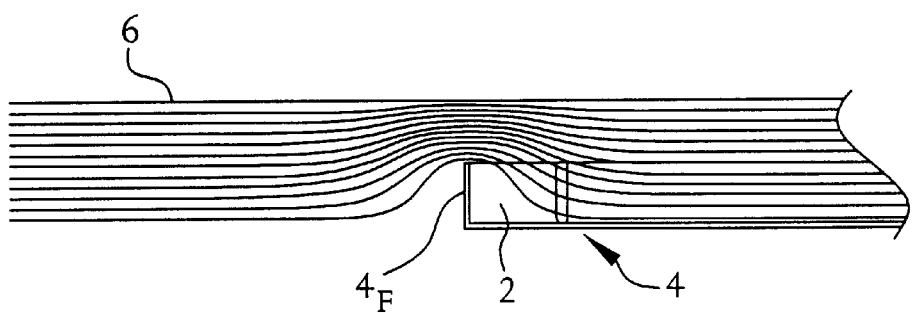
FIG. 2 is a schematic partial cross-sectional view of the tray of FIG. 1 depicting the electrical currents flowing over the front edge of the tray.
Figure 3:
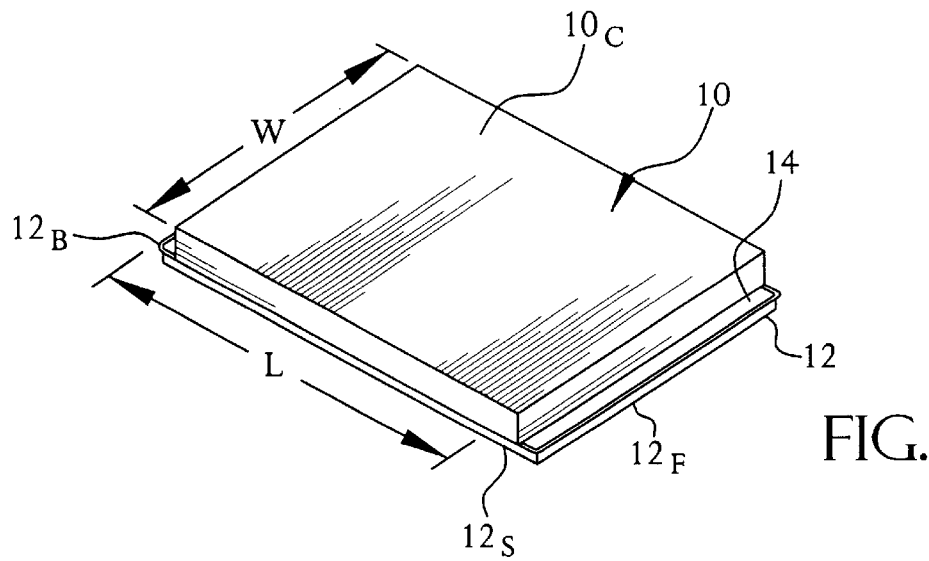
FIG. 3 is an isometric view of a gel running plate according to one embodiment of the invention as it is intended to be positioned on top of a tray containing an electrophoresis gel.

Referring now to the drawings, wherein like reference numerals illustrate corresponding or similar elements throughout the several views, FIG. 3 illustrates one embodiment of a gel running plate 10 according to the present invention as it is intended to be used for covering a tray 12 during an electrophoresis process. The tray 12 includes a conventional electrophoresis gel 14. The tray 12 and running plate 10 combination are intended to be placed on the base of an electrophoresis chamber. The details of the chamber are not important to the description of this invention and are, therefore, omitted from the drawings. The gel described herein is an agarose gel precast into a rectangular slab with one or more transverse rows of wells that extend at least partially through the slab and which are used to contain biological samples to be tested. Gel slabs of this type are well known and come in a variety of sizes and configurations. The particular type of gel is not, however, important to the invention, except to the extent that the size, shape and open areas configuration of the gel running plate will be selected according to the size, shape and well configuration of the gel in light of the teachings provided herein.

Figure 10:
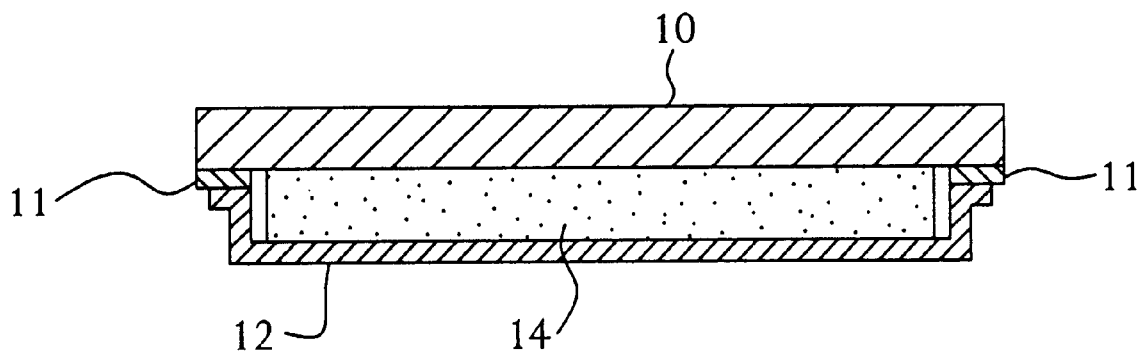
FIG. 10 is a cross-sectional view of an embodiment of the invention that incorporates gaskets to provide an electrical seal between the gel running plate and the tray.

The gel running plate 10 preferably has a shape that is generally the same as the tray 12. For example, as illustrated, conventional gels and trays have a rectangular shape. As such, the gel running plate 10 is similarly configured with a planar rectangular cover surface $10_C$. It is important in the present invention that the width of the gel running plate 10 (designated by the alphanumeric character W in FIG. 3) is at least the same as the width of the tray 12. This permits the gel running plate to rest upon the tray side walls $12_S$. There are two reasons for this. First, the tray side walls $12_S$ support the weight of the gel running plate 10, thus preventing crushing of the electrophoresis gel 14. Second, the gel running plate and side walls $12_S$ form an electrically insulative seal along the sides of the tray, preventing electrical current from flowing in to or out of the tray by way of the sides of the tray. This eliminates the hourglass effect discussed above. Gaskets or sealing strips 11 (shown in FIG. 10) can be added to the gel running plate to further increase the sealing provided between the gel running plate and the side walls $12_S$. The gasket 11 is preferably made from an electrically non-conductive material. In one embodiment of the invention, strips of closed cell silicone foam having a preferred thickness between about 0.010 and 0.25 inches are placed adjacent the side edges of the gel running plate 10 to operate as a gasket. The gasket 11 can also be used to prevent crushing of the gel 14 in situations where the gel 14 is slightly taller than the side walls of the tray (see FIG. 10).

Figure 4:
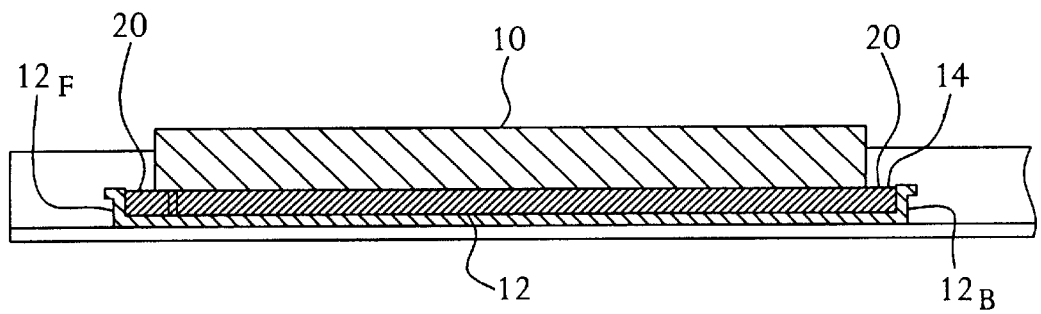
FIG. 4 is a cross-sectional view of gel running plate according to one embodiment of the invention positioned on top of a tray containing an electrophoresis gel during an electrophoresis process.

The length of the gel running plate 10 (designated by the alphanumeric character L in FIG. 3) must be less than the length of the tray 12. More particularly, the length of the gel running plate is preferably shorter than the length of the tray 12 by about twice the depth or height of the tray 12. This allows a spacing or gap 20 between the front and back edges of the tray $12_F$, $12_B$ from the gel running plate 10 that is about the same dimension as the depth of the tray 10 as shown in FIG. 4. For example, conventional gels are generally between about 3 mm to about 8 mm thick, and more specifically between about 5 mm and about 6 mm thick. A tray to hold such a gel would generally have a depth approximately the same as the thickness of the gel. Thus, a gel running plate 10 suitable for use with such a tray would have a length that is about 6 mm to about 16 mm shorter than the tray and, more likely is about 10 mm to about 12 mm shorter. For a typical 10 cm×15 cm gel that is approximately 6 mm thick, a suitable tray 12 is about 10.6 cm wide, about 15 cm long and about 6 mm deep. A preferred running plate 10 for such a gel has about a 10.6 cm width, and a 13.8 cm length.

Figure 5:
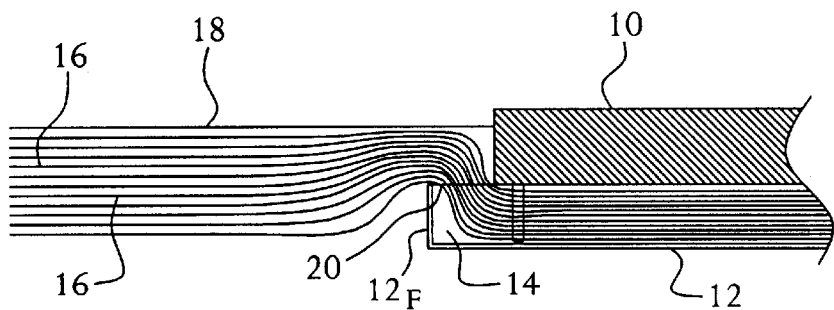
FIG. 5 is a schematic partial cross-sectional view of the tray and gel running plate of FIG. 4 depicting the electrical currents flowing over the front edge of the tray.

Referring to FIG. 5, a partial schematic cross-section of the invention is shown in use. The series of lines 16 depict the flow of electrical current through a buffer solution 18. As the electrical current approaches the front of the tray $12_F$, it begins to flow over the edge. In order to evenly distribute the flow in the gel 12, the gel running plate 12 blocks some if not all of the buffer solution 18 from flowing over the tray 12 and channels the electrical current downward into the tray 12 and gel 14. The effect at the back of the tray is essentially the mirror image of the effect at the front of the tray. Because of the limited spacing provided by the gel running plate 10, the electrical current is forced to flow more uniformly through the gel 14, thereby reducing the formation of tilted bands at the front and back of the gel 14.

The spacing or gap 20 provided at the front and back of the tray 12 can be varied depending on the configuration of the gel. For example, the further the wells are spaced from the leading edge of the gel 14, the larger the gap 20 at the front of the gel can be. However, it is preferred that the gap 20 remain as small as possible, without adversely pinching the current flow into the tray 12 which can slow down the run.

As discussed above, it is desirable to maintain the run times as short as possible. When an electrophoresis test is run with a gel without a tray, the buffer level is kept to a minimum and the majority of the electric current flows generally straight through the gel. This results in a relatively short run time. The use of a conventional tray, however, necessitates the use of additional buffer solution. The additional buffer allows a larger percentage of the electrical current to bypass the gel. As a result the run times are generally longer.

The gel running plate 10 according to the present invention addresses this problem in one embodiment by displacing some, if not all, of the buffer solution from over the tray. As shown in FIG. 5, the gel running plate 10 has a thickness that, when placed in the electrophoresis chamber with the tray 12, results in the top of the gel running plate 10 protruding above the surface of the buffer solution 18. Thus, the electrical charges flowing through the buffer solution are forced to flow through the gel 14. Generally speaking, when using a gel running plate according to the present invention, the height of the buffer solution in the chamber should be about twice the height of the tray so as to provide a current path that passes over the edge of the tray that is at least equal to the current path in the tray. Thus, generally speaking, the gel running plate 10 should be at least as thick as the height of the tray 12.

Figure 9:
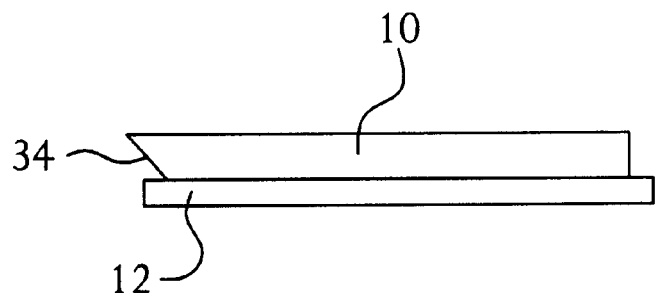
FIG. 9 is a side view of a further embodiment of a gel running plate with a sloped leading edge for controlling electrical current flow.

It may also be beneficial to angle the leading edge 34 of the gel running plate to assist in channeling the electrical current into the tray. This embodiment of the invention is shown in FIG. 9.

There are certain situations where it is desirable create current gradients within the gel during a run. In a conventional electrophoresis process, this is accomplished by tilting the whole gel chamber so that the tray is exposed to different levels of buffer solution, and hence electric current, in the direction of the desired gradient. The primary deficiencies with this method are that it is difficult to reproduce accurately and is very cumbersome.

Figure 6:
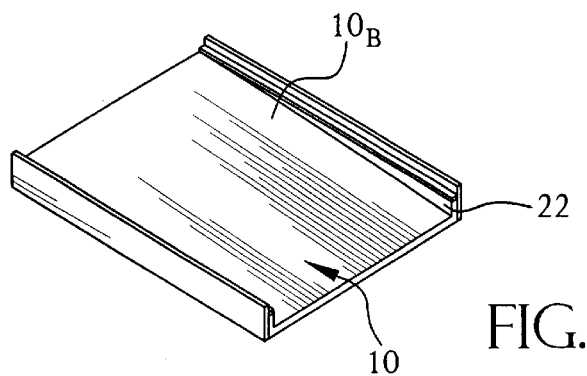
FIG. 6 is an isometric view of the bottom of a gel running tray according to one embodiment of the invention which, when in use, provides a bottom surface which is not parallel with the top surface of the gel.

One embodiment of the present invention provides a solution to this problem. Referring to FIG. 6, a version of the gel running plate 10 is shown which has a tapered bottom surface $10_B$ such that when placed on the tray the bottom surface is not parallel with the top surface of the gel. As such, the tapered gel running plate 10 varies the amount of buffer solution located above the gel, thereby providing an accurate and consistent gradient run without having to tilt the chamber. As shown, the tapering of the bottom surface $10_B$ results in sidewall portions 22 which are designed to maintain sealing contact between the running plate 10 and the tray 12. This embodiment of the invention also allows for different gradients to be run on the same gel by providing different tapers on different portions of the underside of the gel running plate. Curved, stepped or other non-linear gradients can be formed by changing the shape of the underside of the gel running plate. It is also contemplated that, instead of tapering or shaping the bottom surface of the gel running plate, the gaskets 11 could be tapered or tapered shims could be inserted between the gel running plate 10 and the side walls of the tray 12.

Figure 6A:
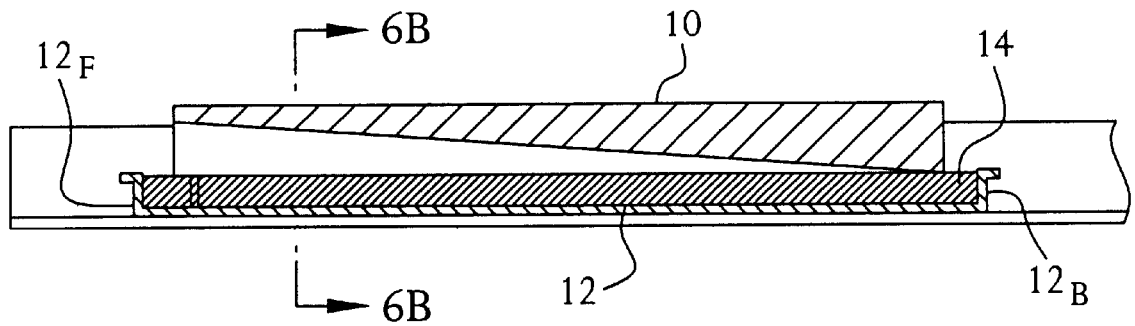
FIG. 6A is a cross-sectional view of the tapered gel running plate of FIG. 6 as it is intended to be positioned on a tray during an electrophoresis process.
Figure 6B:
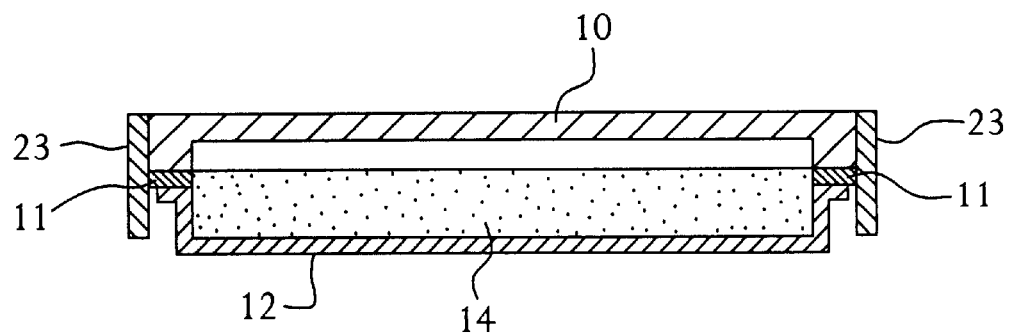
FIG. 6B is a cross-sectional view of the tapered gel running plate of FIG. 6A taken along lines 6B—6B.

As shown in FIGS. 6 and 6B, it may also be desirable to include side rails 23 which are designed to be located along the sides of the tray 12 when the gel running plate 10 is positioned on the tray 12. These rails 23 assist in the placement and proper positioning of the gel running plate 10 on the tray 12. The side rails 23 can be utilized with the gel running plate 10 whether or not it is tapered. While the side rails 23 are shown as separately attached to the gel running plate 10, it is also contemplated that they can be formed as an integral part of the gel running plate 10. The side rails 23 in this embodiment preferably do not extend past the bottom of the tray, thereby avoiding contact with the chamber floor since such contact would lessen the seal between the gel running plate 10 and the tray 12.

It is also contemplated that the gel running plate 10 can be constructed simply as a thin non-conductive sheet that is sized as discussed above without respect to thickness. In this form of the invention, the sheet preferably adheres or is attached to the side walls $12_S$ of the tray to prevent electrical flow into the tray from the side. In one variation, the thin sheet has channel shaped flanges on the side that slide over the flange on the side walls $12_S$ of the tray. This embodiment of the gel running plate eliminates or reduces the tilting and hourglassing of the bands that would otherwise develop.

Another problem that exists in a conventional electrophoresis process is the build-up of heat during operation. As the process is run on a gel, heat develops in the gel and the buffer solution. The faster that the process is run, the more heat is generated. At the same time, the warmer the solution and gel, the faster the macromolecules will move through the gel. As a consequence, if temperature gradients develop in the gel or buffer solution, the samples tend to migrate faster in the warmer portions producing band abnormalities.

It is contemplated that the gel running plate 10 of the present invention can be configured to address this problem. For example, in one embodiment of the invention, the gel running plate 10 includes a chamber that is filled with a cooling liquid to help cool the gel. In another embodiment cooling liquid is circulated through the gel running plate 10. It should be readily apparent that the gel running plate should be designed to be as conductive as possible while, at the same time, maintaining the gel running plate's electrically insulative properties.

Figure 7A:
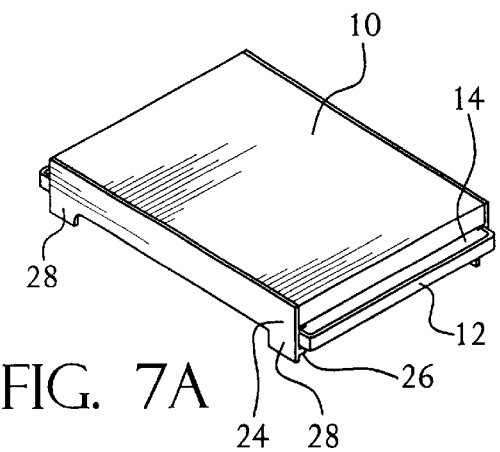
FIGS. 7A–7B are isometric views of a gel running plate according to another embodiment of the invention wherein the tray is supported off the floor of the chamber by the gel running plate and is slidable with respect to the plate.
Figure 7B:
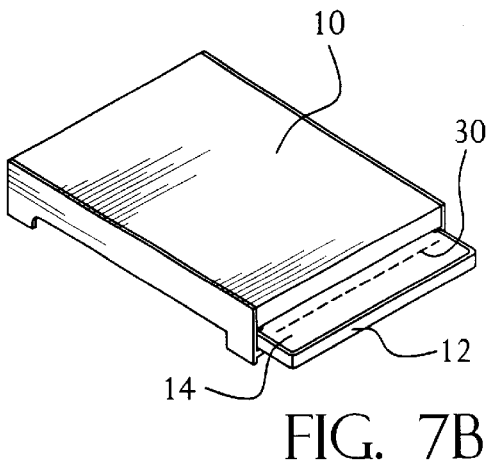

Another way to improve the cooling of a gel in a tray is to configure the gel running plate 10 to lift the tray 12 off the chamber bottom. This would permit the buffer solution to function as a cooling medium under the tray 12. FIG. 7A illustrates one version of this embodiment. In this version, the gel running plate 10 includes side supports 24 that extend down from the plate. The side supports 24 preferably include a ridge or flange 26 that is positioned so as to form a channel into which the tray slides. The side supports 24 also include leg portions 28 which extend beyond the tray 12 so as to position the tray off the bottom of the chamber. The channel permits the tray to be slid outward from the gel running plate as shown in FIG. 7B, thereby permitting access to the wells 30 for loading the samples. The side supports 24 provide the added benefit of inhibiting electric current flow into the tray through the sides in situations where the seal between the gel running plate 10 and the tray 12 is not sufficient.

It is also contemplated that a separate ribbed base plate can be utilized in the present invention under the tray 12. The ribs would preferably extend across the width of the base plate (perpendicular to the current flow) so as to inhibit current flow under the tray.

Figure 8:
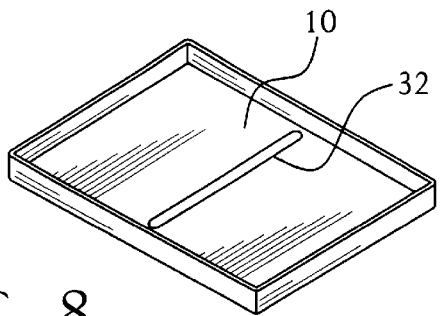
FIG. 8 is an isometric view of another embodiment of the gel running plate for use with a multi-tiered gel.

While the above discussion has been generally directed to a gel running plate for a conventional gel with a single tier of wells, it is also contemplated that the present invention can be used in a gel with two or more tiers of wells. In such an embodiment, it may be desirable to include a slot in the gel running plate at the location of the second tier of wells to permit access for placement of the biological samples. An embodiment of the invention showing the slot 32 formed in the gel running plate 10 is depicted in FIG. 8. This embodiment also shows a variation on the configuration of the gel running plate. Instead of forming the entire gel running plate with a uniform thickness that protrudes above the buffer solution as shown in FIGS. 4 and 5, in this embodiment the gel running plate 10 includes upwardly extending walls which inhibit the buffer solution from flowing over the plate 10. As a consequence, less material is needed to form the plate 10.

Figure 11:
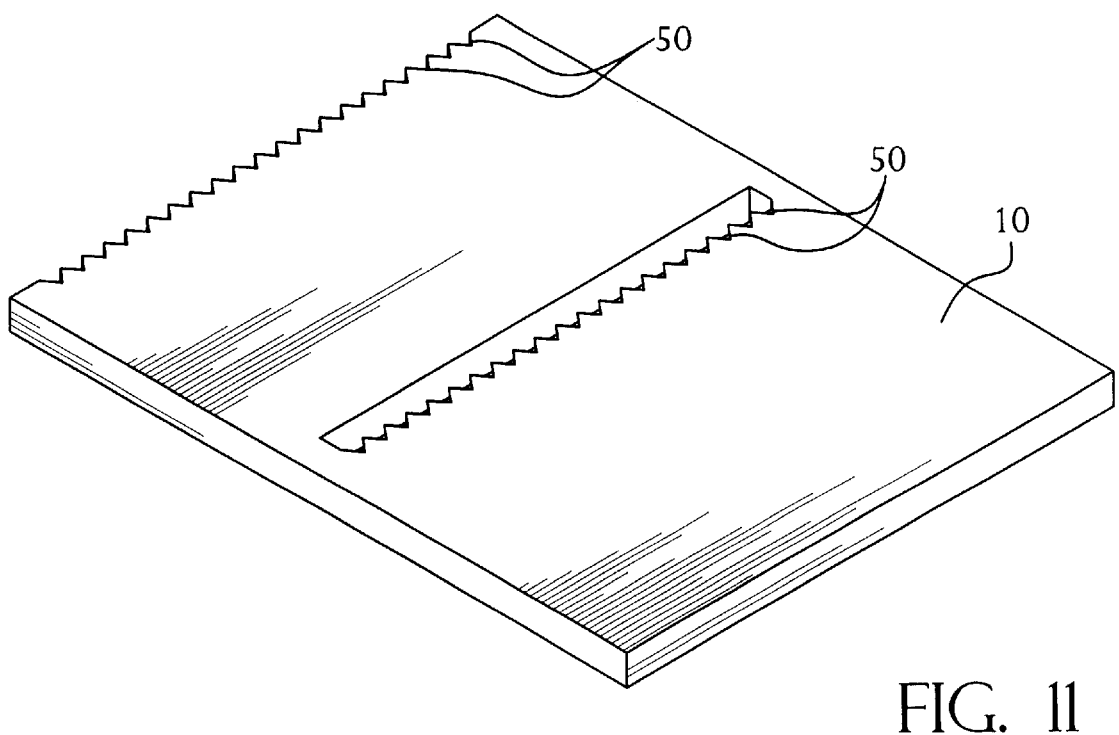
FIG. 11 is an isometric view of another embodiment of the gel running plate illustrating the incorporation of V-shaped notches for guiding pipette tips during sample loading.
Figure 12:
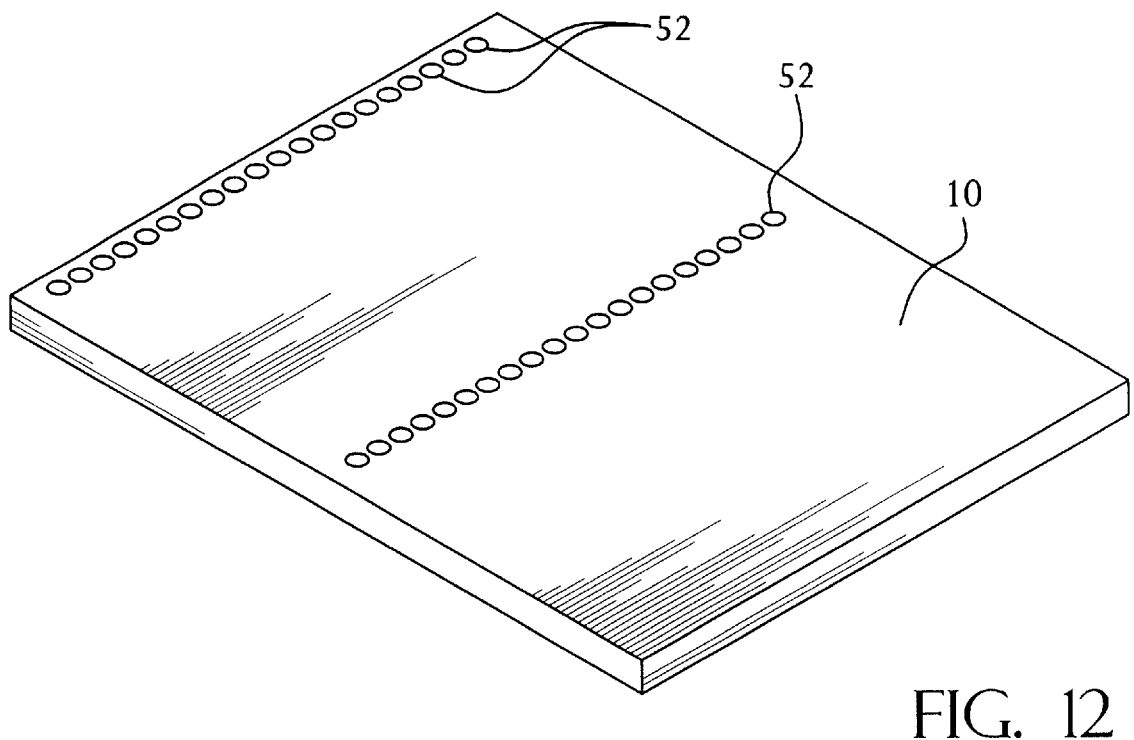
FIG. 12 is an isometric view of yet another embodiment of the gel running plate illustrating the incorporation of circular holes for guiding pipette tips during sample loading.

Two further embodiments of the invention are shown in FIGS. 11 and 12. In these embodiments, the gel running plate 10 is designed to facilitate loading of the wells by guiding the pipette tips that are used to dispense the samples. As shown in FIG. 11, a series of V-shaped notches 50 are formed in the gel running plate 10. Each V-shaped notch is suitably positioned to guide a pipette tip toward an associated well when the gel running plate 10 is positioned on top of the gel. Similarly, in FIG. 12 a series of holes 52 are formed through the gel running plate 10 and positioned such that each hole aligns with a corresponding well when the gel running plate is positioned on top of a gel. This embodiment of the invention assists in minimizing damage to the fragile wells that can occur during loading of the samples, especially when unwieldy, multi-tip pipetters are used.

Although not shown in the figures, it is also contemplated that a handle can be added onto the gel running plate to facilitate placement and removal.

As noted above, it is preferable that the gel running plate 10 is made from an electrically non-conductive material to properly control electrical current flow into and out of the tray. One suitable material for use in the present invention is plastic. However, those skilled in the art would readily be capable of substituting alternate materials in the present invention in light of the teachings provided herein.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

What is claimed is:

1. A gel running plate in combination with a tray and an electrophoresis gel for use in an electrophoresis process, the plate adapted to cover the electrophoresis gel within the tray and to effect flow for electrical current into and out of the tray, the plate being separatable from the tray and having a length dimension that is less than a length dimension of the tray such that gaps exist between the front and back of the plate and the tray when the plate is positioned on the tray, and the plate having a width dimension that is at least as wide as the width dimension of the tray such that the plate rest upon the tray when the plate is positioned on the tray.

2. A gel running plate according to claim 1 wherein the plate includes a planar surface.

3. A gel running plate according to claim 1 wherein the plate includes a plurality of guides for aligning and guiding pipette tips during sample loading.

4. A gel running plate for use in an electrophoresis process to cover an electrophoresis gel located within a tray, the plate adapted to effect flow of electrical current into and out of the tray, the plate having a length dimension that is less than a length dimension of the tray such that gaps exist between the front and back of the plate and the tray when the plate is positioned on the tray, and the plate having a width dimension that is at least as wide as the width dimension of the tray such that the plate rests upon the tray when the plate is positioned on the tray, and wherein the plate includes sealing strips located on opposed sides of the plate and adapted to engage with side walls on the tray.

5. A gel running plate according to claim 4 wherein the sealing strips are made from closed cell silicone foam.

6. A gel running plate according to claim 5 wherein the sealing strips have a thickness between about 0.010 inches and about 0.25 inches.

7. A gel running plate according to claim 4 wherein the length dimension of the plate is shorter than the length dimension of the tray by a dimension equal to about twice the height of the tray over which the plate is to be positioned such that when the plate is centered over the tray there are gaps between the front and back of the plate and the tray that have a dimension equal to about one tray height.

8. A gel running plate according to claim 4 wherein the plate includes a bottom surface adapted to be positioned over a gel when the gel running plate is positioned on a tray, and side edges which are adapted to engage side walls on the tray when the gel running plate is positioned on a tray, and wherein at least a portion of the bottom surface and the side edges lie along planes which form an angle with respect to one another, such that when the gel running plate is positioned on the tray at least a portion of the bottom surface is at an angle with respect to the gel.

9. A gel running plate according to claim 8 wherein the entire bottom surface is at an angle to the side edges.

10. A gel running plate according to claim 8 wherein the side edges include gaskets for forming a seal with the tray.

11. A gel running plate according to claim 10 wherein gaskets are tapered which produces the angle between the bottom surface and the side edges.

12. A gel running plate according to claim 4 wherein the plate includes a cooling medium.

13. A gel running plate according to claim 12 wherein the cooling medium is circulated through the plate.

14. A gel running plate for use in an electrophoresis process to cover an electrophoresis gel located within a tray, the plate adapted to effect flow of electrical current into and out of the tray, the plate having a length dimension that is less than a length dimension of the tray such that gaps exist between the front and back of the plate and the tray when the plate is positioned on the tray, and the plate having a width dimension that is at least as wide as the width dimension of the tray such that the plate rests upon the tray when the plate is positioned on the tray, the plate including a planar surface and wherein the plate includes side rails which extend downward from the planar cover surface and are spaced apart a distance greater than the width of the tray such that the tray is located between the side rails when the plate is positioned on top of the tray.

15. A gel running plate according to claim 14 further comprising flanges formed on the side rails and adapted to engage with the tray to permit the tray to slide with respect to the plate, the side rails having a vertical height which locates the tray off the ground when the tray is engaged with the flanges on the plate.

16. A gel running plate for use in an electrophoresis process to cover an electrophoresis gel located within a tray, the plate adapted to effect flow of electrical current into and out of the tray, the plate having a length dimension that is less than a length dimension of the tray such that gaps exist between the front and back of the plate and the tray when the plate is positioned on the tray, and the plate having a width dimension that is at least as wide as the width dimension of the tray such that the plate rests upon the tray when the plate is positioned on the tray, and further comprising flanges formed on the plate and adapted to engage with flanges formed on the tray for permitting the tray to slide with respect to the plate.

17. A device for use in an electrophoresis process to cover an electrophoresis gel and effect current flow through the gel, the device comprising:

a tray having a base, an upstanding front wall, back wall and opposed side walls, the tray containing an electrophoresis gel, the tray having a length dimension and a width dimension; and a gel running plate adapted to be placed on the tray to cover the electrophoresis gel within the tray during an electrophoresis process, the gel running plate being separatable from the tray and having a length dimension that is less than a length dimension of the tray such that a gap exists between the tray and the plate when the plate is positioned on the tray, and a width dimension at least as wide as the width dimension of the tray such that the plate rests upon the opposed side walls of the tray when the plate is positioned on the tray.

18. A device according to claim 17 wherein the length dimension of the plate is shorter than the length dimension of the tray by a dimension equal to about twice the height of the tray over which the plate is to be positioned such that when the plate is centered over the tray there are gaps between the front and back of the plate and the tray that have a dimension equal to about one tray height.

19. A device according to claim 18 wherein the gel running plate includes a bottom surface adapted to be positioned over a gel when the gel running plate is located on the tray, and side edges which engage with the side walls of the tray when the gel running plate is located on the tray, wherein at least a portion of the bottom surface is at an angle to the side walls of the tray such that the at least a portion of the bottom surface is skewed with respect to the tray when the plate is positioned on the tray.

20. A device according to claim 19 wherein the entire bottom surface is linearly skewed with respect to the tray when the plate is positioned on the tray.

21. A device according to claim 17 further comprising flanges formed on the plate and adapted to engage with flanges formed on the tray for permitting the tray to slide with respect to the plate.

22. A device according to claim 17 wherein the plate includes a cooling medium.

23. A device according to claim 22 wherein the cooling medium is circulated through the plate.

24. A device according to claim 17 wherein the gel running plate includes a plurality of guides for aligning and guiding pipette tips during sample loading.

25. A device for use in an electrophoresis process to cover an electrophoresis gel and effect current flow through the gel, the device comprising:

a tray having a base, an upstanding front wall, back wall and opposed side walls, the tray adapted to contain an electrophoresis gel, the tray having a length dimension and a width dimension; and a gel running plate adapted to be placed on the tray during an electrophoresis process, the gel running plate having a length dimension that is less than a length dimension of the tray such that a gap exists between the tray and the plate when the plate is positioned on the tray, and a width dimension at least as wide as the width dimension of the tray such that the plate rests upon the opposed side walls of the tray when the plate is positioned on the tray;

wherein the plate includes sealing strips located on opposed sides of the plate, the sealing strips adapted to contact the side walls on the tray to form a seal therebetween.

26. A device according to claim 25 wherein the sealing strips are made from closed cell silicone foam.

27. A device according to claim 26 wherein the sealing strips have a thickness between about 0.010 inches and about 0.25 inches.

28. A device for use in an electrophoresis process to cover an electrophoresis gel and effect current flow through the gel, the device comprising:

a tray having a base, an upstanding front wall, back wall and opposed side walls, the tray adapted to contain an electrophoresis gel, the tray having a length dimension and a width dimension; and a gel running plate adapted to be placed on the tray during an electrophoresis process, the gel running plate having a length dimension that is less than a length dimension of the tray such that a gap exists between the tray and the plate when the plate is positioned on the tray, and a width dimension at least as wide as the width dimension of the tray such that the plate rests upon the opposed side walls of the tray when the plate is positioned on the tray;

wherein the plate includes a planar cover with side rails that extend downward from the cover, the side walls being spaced apart a distance greater than the width of the tray such that the tray is located between the side rails when the plate is positioned on top of the tray.

29. A device according to claim 28 further comprising flanges formed on the side rails and adapted to engage with the tray to permit the tray to slide with respect to the plate, the side rails having a vertical height which locates the tray off the ground when the tray is engaged with the flanges on the plate.

30. A method for controlling electrical current flow into an out of a tray in an electrophoresis process, the method comprising the steps of:

placing a tray containing an electrophoresis gel into an electrophoresis chamber, the gel containing biologic samples within wells, the tray having a front wall, a back wall, and opposed side walls;

adding buffer solution into the chamber;

placing a gel running plate on top of the tray such that the gel running plate rests on the side walls but is spaced apart from the front and back walls leaving a gap therebetween, the gel running plate having a height sufficient to protrude above the buffer solution; and applying voltage to buffer solution so that an electrical current is generated, the electrical current producing migration of the samples within the gel.

* * * * *